United States Patent
Gupta et al.

(10) Patent No.: US 9,626,521 B2
(45) Date of Patent: Apr. 18, 2017

(54) PHYSIOLOGICAL SIGNAL-BASED ENCRYPTION AND EHR MANAGEMENT

(71) Applicants: Sandeep Gupta, Phoenix, AZ (US); Ayan Banerjee, Tempe, AZ (US)

(72) Inventors: Sandeep Gupta, Phoenix, AZ (US); Ayan Banerjee, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 71 days.

(21) Appl. No.: 14/688,181

(22) Filed: Apr. 16, 2015

(65) Prior Publication Data

US 2015/0304101 A1    Oct. 22, 2015

Related U.S. Application Data

(60) Provisional application No. 61/980,374, filed on Apr. 16, 2014.

(51) Int. Cl.
G06F 21/00 (2013.01)
G06F 21/60 (2013.01)
(Continued)

(52) U.S. Cl.
CPC .......... *G06F 21/606* (2013.01); *H04L 9/0866* (2013.01); *H04W 12/02* (2013.01);
(Continued)

(58) Field of Classification Search
CPC ............... G06F 21/606; G06F 21/62; G06F 2221/2107; H04L 9/00; H04L 63/0428;
(Continued)

(56) References Cited

U.S. PATENT DOCUMENTS

| 6,728,576 B2 | 4/2004 | Thompson et al. |
| 7,171,680 B2 | 1/2007 | Lange |

(Continued)

FOREIGN PATENT DOCUMENTS

| EP | 1284149 A2 | 2/2003 |
| EP | 2294978 A1 | 9/2010 |

(Continued)

OTHER PUBLICATIONS

Yu et al. (2010). "Ecg monitoring over bluetooth: Data compression and transmission," WCNC, IEEE 2010, 1-5.
(Continued)

*Primary Examiner* — Yogesh Paliwal
(74) *Attorney, Agent, or Firm* — Michael Best & Friedrich LLP

(57) ABSTRACT

Systems and methods are provided for encoding and decoding data (such as, for example, an encryption key) using a physiological signal. A data item string is separated into a defined number of component segments and each component segment is used as a coefficient of a polynomial equation. A plurality of signal features are then identified from a physiological signal and a plurality of ordered pairs are created based on the plurality of identified signal features using the polynomial equation. A data package including the plurality of ordered pairs and obfuscated by a plurality of chaff points is transmitted to another system. The receiver system uses a corresponding physiological signal to filter out the chaff points and to reconstruct the polynomial equation, for example, by LaGrangian interpolation. The coefficients of the reconstructed polynomial equation are then used to derive the encoded data item string.

18 Claims, 12 Drawing Sheets

(51) Int. Cl.
*H04W 12/02* (2009.01)
*H04L 9/08* (2006.01)
*H04L 29/06* (2006.01)
*H04B 13/00* (2006.01)
*H04W 4/00* (2009.01)
*H04W 12/04* (2009.01)
*A61B 5/00* (2006.01)

(52) U.S. Cl.
CPC .... *A61B 5/0004* (2013.01); *G06F 2221/2107* (2013.01); *H04B 13/005* (2013.01); *H04L 63/0428* (2013.01); *H04L 2209/34* (2013.01); *H04L 2209/805* (2013.01); *H04L 2209/88* (2013.01); *H04W 4/008* (2013.01); *H04W 12/04* (2013.01)

(58) Field of Classification Search
CPC ..... H04W 12/02; H04W 12/04; H04W 4/008; A61B 5/0004; H04B 13/005
USPC .......................................................... 380/28
See application file for complete search history.

(56) References Cited

U.S. PATENT DOCUMENTS

| | | | |
|---|---|---|---|
| 7,289,761 | B2 | 10/2007 | Mazar |
| 7,826,540 | B2 | 11/2010 | Melick et al. |
| 7,827,011 | B2 | 11/2010 | DeVaul et al. |
| 7,978,062 | B2 | 7/2011 | LaLonde et al. |
| 7,978,081 | B2 | 7/2011 | Shears et al. |
| 2002/0164056 | A1* | 11/2002 | Funada .............. G06K 9/00067 382/124 |
| 2006/0025697 | A1 | 2/2006 | Kurzweil et al. |
| 2008/0228094 | A1 | 9/2008 | Audet et al. |
| 2009/0125084 | A1* | 5/2009 | Juels .................... A61B 5/0031 607/60 |
| 2009/0310779 | A1* | 12/2009 | Lam .................. G06K 9/00093 380/46 |
| 2010/0036268 | A1 | 2/2010 | Ferren et al. |
| 2010/0082302 | A1 | 4/2010 | Garudadri et al. |
| 2010/0106269 | A1 | 4/2010 | Garudadri et al. |
| 2010/0121406 | A1 | 5/2010 | Libbus et al. |
| 2010/0211594 | A1 | 8/2010 | Penders et al. |
| 2010/0298664 | A1 | 11/2010 | Baumann et al. |
| 2010/0303101 | A1 | 12/2010 | Lazar et al. |
| 2010/0331711 | A1 | 12/2010 | Krauss et al. |
| 2011/0040200 | A1 | 2/2011 | Douglas et al. |
| 2011/0066010 | A1 | 3/2011 | Moon et al. |
| 2011/0092834 | A1 | 4/2011 | Yazicioglu et al. |
| 2011/0319769 | A1 | 12/2011 | Hedberg et al. |
| 2012/0151205 | A1* | 6/2012 | Raykova ................ H04L 9/085 713/150 |
| 2013/0317377 | A1 | 11/2013 | Gupta et al. |

FOREIGN PATENT DOCUMENTS

| | | |
|---|---|---|
| EP | 2298164 A2 | 3/2011 |
| WO | 2008097652 A2 | 8/2008 |
| WO | 2008151818 A2 | 12/2008 |
| WO | 2009032134 A2 | 3/2009 |
| WO | 2010036894 A2 | 4/2010 |
| WO | 2010036897 A1 | 4/2010 |
| WO | 2010037056 A1 | 4/2010 |
| WO | 2010135482 A1 | 11/2010 |
| WO | 2011082341 A1 | 12/2010 |
| WO | 2011032030 A1 | 3/2011 |
| WO | 2011034881 A1 | 3/2011 |

OTHER PUBLICATIONS

McSharry et al. (2003). "A dynamical model for generating synthetic electrocardiogram signals," IEEE Transactions on Biomedical Engineering, 50, 289-294.

Chou et al. (2005). "A Novel QRS Detection algorithm applied to the analysis of heart rate variability of patients with sleep apnea," Biomedical Eng. Application, Basis & communication, 17, 259-63.
Jafari et al. (2006). "Adaptive electrocardiogram feature extraction on distributed embedded systems," IEEE Transactions on Parallel and Distributed Systems, 17, 797-807.
Eduardo et al. (2010). "Implementation of Compressed Sensing in Telecardiology Sensor Networks," International Journal of Telemedicine and Applications, 2010, 1-12.
Kim et al. (2008). "DWLT compression method based on MSVQ for a real-time ECG monitoring system in WSNs," Proceedings of the Int. Conf. on Mobile Tech., App. and Systems. ACM, 1-5.
Zigel et al. (2002). "The weighted diagnostic distortion (WDD) measure for ECG signal compression,", IEEE Transactions on Biomedical Engineering , 47, 1422-1430.
Cheng et al. (2003). "Evaluating probabilistic queries over imprecise data," Proceedings of SIGMOD Conf., 1-13.
Chu et al. (2002). " Scalable information-driven sensor querying and routing for ad hoc heterogeneous sensor networks," Journal of High Performance Computing Applications.
Deshpande et al. (2001). "Independence is Good: Dependency-Based Histogram Synopses for High-Dimensional Data," ACM SIGMOD, 199-210.
Deshpande et al. (2004). "Exploiting correlated attributes in acquisitional query processing," Technical report, Intel-Research, Berkeley.
Getoor et al. (2001). "Selectivity estimation using probabilistic models," ACM SIGMOD, May, 1-12.
Gibbons. (2001). "Distinct sampling for highly-accurate answers to distinct values queries and event reports," In Proc. of VLDB, Sep. 2001.
Gibbons et al. (1998). "New sampling-based summary statistics for improving approximate query answers," SIGMOD, 1-12.
Hellerstein et al. (1999). "Interactive data analysis with CONTROL," IEEE Computer, 32(8), 51-58.
Hellerstein et al. (1997). "Online aggregation," In SIGMOD, May, 171-182.
Intanagonwiwat et al. (2000). "Directed diffusion: A scalable and robust communication paradigm for sensor networks," In MobiCOM, 56-67.
Kollios et al. (2004). "Approximate aggregation techniques for sensor databases," ICDE 2004, 1-12.
Lerner et al. (2002). "Monitoring a complex physical system using a hybrid dynamic bayes net," UAI.
Lin et al. (1971). "An effective heuristic algorithm for the tsp. Operations Research," 21,498-516.
Madden. (2003) "The design and evaluation of a query processing architecture for sensor networks," Master's thesis, UC Berkeley.
Madden et al. (2003). "The design of an acquisitional query processor for sensor networks," ACM SIGMOD, 1-12.
Olston et al. (2002). "Best effort cache sychronization with source cooperation," SIGMOD, 1-27.
Olston et al. (2001). "Adaptive precision setting for cached approximate values," ACM SIGMOD, May, 1-12.
Pottie et al. (2000). "Wireless integrated network sensors," Communications of the ACM, 43(5), 51-58.
Yao et al. (2003). "Query processing in sensor networks," Conference on Innovative Data Systems Research (CIDR), 1-12.
Jalaleddine et al. (1990). "ECG data compression techniques-a unified approach," IEEE Transactions on Biomedical Engineering, 37(4), 329-343.
Nabar et al. (2011). "GeM-REM: Generative Model-driven Resource e cient ECG Monitoring in Body Sensor Networks," In Proceedings of International Conference on Body Sensor Networks (BSN). IEEE, 1-12.
Nabar et al. (2011). "Resource-e cient and Reliable Long Term Wireless Monitoring of the Photoplethysmographic Signal," Wireless Health 2011. IEEE, http://ee.washington.edu/research/nsl/papers/PPG.pdf.
Reddy et al. (2009). "Use of fourier series analysis for motion artifact reduction and data compression of PPG signals," IEEE Transactions on Instrumentation and Measurement, 58(5), 1706-1711.

(56) References Cited

OTHER PUBLICATIONS

Bagade et al. (2013). "Protect your BSN: No Handshakes, just Namaste!," in Body Sensor Networks (BSN), 2013 IEEE International Conference on , vol., No., pp. 1-6, May 6-9, 2013.
Banerjee et al. (2013). "PEES: physiology-based end-to-end security for mHealth," Proceedings of the 4th Conference on Wireless Health, p. 1-8, Nov. 1-3, 2013, Baltimore, Maryland.
Sorber et al. (2012). "An amulet for trustworthy wearable mHealth," Proceedings of the Twelfth Workshop on Mobile Computing Systems & Applications, Feb. 28-29, 2012, San Diego, California.
Sahoo (2012). "Efficient Security Mechanisms for mHealth Applications Using Wireless Body Sensor Networks." Sensors 12, No. 9: 12606-12633.
Tan et al. (2009). "IBE-Lite: a lightweight identity based cryptography for body sensor networks ," IEEE Transactions on Information Technology in Biomedicine, vol. , 2009.
Venkatasubramanian et al. (2010). "PSKA: Usable and Secure Key Agreement Scheme for Body Area Networks," in Information Technology in Biomedicine, IEEE Transactions on , vol. 14, No. 1, pp. 60-68, Jan. 2010.
Venkatasubramanian et al. (2010). "Physiological value-based efficient usable security solutions for body sensor networks," ACM Trans. Sen. Netw. 6, 4, Article 31 (Jul. 2010).
Valdes et al. (2000). "Adaptive, Model-Based Monitoring for Cyber Attack Detection," Proceedings of the Third International Workshop on Recent Advances in Intrusion Detection.
Lemay et al. (2011). "Model-based Security Metrics Using ADversary VIew Security Evaluation (ADVISE)," in Quantitative Evaluation of Systems (QEST), 2011 Eighth International Conference on , vol., No., pp. 191-200, Sep. 5-8, 2011.
Ritchey et al. (2000). "Using model checking to analyze network vulnerabilities," in Security and Privacy, 2000. S&P. 2000. Proceedings. 2000 IEEE Symposium on , vol., No., pp. 156-165, 2000.
Morais et al. (2011). "A model-based attack injection approach for security validation," Proceedings of the 4th international conference on Security of information and networks.
Morchon et al. (2006). "Resource-efficient security for medical body sensor networks", Int. Wksp. on Wearable and Implantable Body Sensor Networks, 2006.
Cherukuri et al. (2003). "Biosec: a biometric based approach for securing communication in wireless networks of biosensors implanted in the human body," in Parallel Processing Workshops, 2003. Proceedings. 2003 International Conference on , vol., No., pp. 432-439, Oct. 6-9, 2003.
Jiang et al. (2007). "An automatic analysis method for detecting and eliminating ECG artifacts in EEG," Comput Biol Med. Nov. 2007;37(11):1660-71.
Liu et al. (2008). "TinyECC: A Configurable Library for Elliptic Curve Cryptography in Wireless Sensor Networks," in Information Processing in Sensor Networks, 2008. IPSN '08. International Conference on , vol., No., pp. 245-256, Apr. 22-24, 2008.
Malhotra et al. (2007). "Implementation of Elliptic-Curve Cryptography on Mobile Healthcare Devices," in Networking, Sensing and Control, 2007 IEEE International Conference on , vol., No., pp. 239-244, Apr. 15-17, 2007.
Poon et al. (2006). "A novel biometrics method to secure wireless body area sensor networks for telemedicine and m-health," in Communications Magazine, IEEE , vol. 44, No. 4, pp. 73-81, Apr. 2006.

\* cited by examiner

PHYSIOLOGICAL SIGNAL-BASED ENCRYPTION AND EHR MANAGEMENT

RELATED APPLICATIONS

This application claims the benefit of U.S. Provisional Application No. 61/980,374, filed on Apr. 16, 2014 and entitled "PEHR-MAN: Physiology Based Life-Long EHR Management," the entire contents of which are incorporated herein by reference.

STATEMENT REGARDING FEDERALLY SPONSORED RESEARCH OR DEVELOPMENT

This invention was made with government support under grants 0831544 and 1116385 awarded by the National Science Foundation. The government has certain rights in the invention.

BACKGROUND

The present invention relates to mechanisms for secured communication between two or more devices/systems. In particular, the present invention relates to systems and methods that utilize physiological signals to encode secret data.

The current way of managing electronic health records (EHRs) has several key drawbacks, which cannot be sustained as the number of disparate health records for a patient increases over time. Setting up an EHR requires the patient to create a username and a password with an EHR provider or with the application used in the smartphone. Password based security in practice fails to provide adequate levels of privacy (enterprise security initiatives like FIDO are switching away from passwords) and can be easily forgotten given the large number of EHRs that an individual may maintain throughout his lifetime leading to loss of useful health data. Collating data from the disparate EHRs to create a comprehensive health history is therefore not easy. For the patients at the very least this requires managing usernames and passwords at for each of the EHR that they have. This is not scalable. On the clinical side, this requires filling out cumbersome paperwork from one health system to the other causing considerable delays in diagnosis and treatment of a patient. Such delays can be especially inconvenient when the user is in need of emergency care. Another problem with our current approach of EHR management is that the health records have to be increasingly maintained for the entire lifetime of the patient. This imposes considerable burden on the system to keep patient data private, which often transforms into a long-term password maintenance nightmare and regular password changes. What is required is a more seamless scheme of ensuring the privacy of the disparate patient EHRs and make them available as needed.

The Health Insurance Portability and Accountability Act (HIPAA) rules any form of personally identifiable health information has to be secured. Hence the data collection phase requires a secure communication channel from the sensors to the smartphone and subsequently to the EHR. However, compliance to the HIPAA rules should not impose a high cognitive load on the user and has to be done implicitly in a fast and transparent way.

SUMMARY

Given the real time nature of the assessment and suggestion modules of our architecture, health data reconciliation has to be fast. However, HIPAA rules of privacy have to be maintained during the reconciliation process as well. Traditional methods of granting EHR access through username and password will surely not work in a real-time proactive setting. Further, open access to EHR whenever required is not HIPAA compliant.

In various embodiments, the invention provides systems and methods that use time-varying physiological signal features to ensure privacy of data communication as well as storage in EHRs in a way that it is transparent to the users, in that they do not have to perform any specific action (e.g., security configuration such as password entry) to secure the data transfer to the EHR. Some embodiments utilize generative models that represent physiological signals with two types of parameters: a) slow varying repetitive morphological features, and b) highly varying temporal features. Some such embodiments utilize generative models of PPG and/or ECG signals can be used to implement end-to-end security from the sensors directly to the EHRs.

In some embodiments, generative signal models are used as unique physiological signatures of a specific person to facilitate fast authenticated reconciliation of EHRs. In this technique, whenever the assessment module needs to reconcile multiple EHRs, it will sample the given physiological signal and derive its generative model using a curve fitting procedure. The assessment module can then use the synthesized physiological signals to perform PPA with multiple EHRs and establish a HIPAA compliant communication channel through which it can reconcile the data. Thus, HIPAA compliant reconciliation is transparent to the user.

In some embodiments, the invention includes a non-invasive method for life long end-to-end management of electronic health records (EHR), from body worn sensors to the cloud servers, using physiological signals. The technique may use physiological signals and models of the signals to automatically manage (i.e., create, access, fuse, and omit) EHRs associated with a given user in an authenticated privacy ensured manner. At the time of EHR creation (potential at time of birth) the doctor with the help of proposed system samples the person's (baby's) physiological signals and trains a generative model and uses the model parameters to create an EHR. After the initialization step, the sensors on the user use current physiological signal samples to encrypt secrets and transfer them to the cloud server where the EHR is hosted. The EHR uses the generative model to generate physiological signal samples and then uses the model generated signal to decrypt the secret. This secret is then used to encrypt further health record data and to update person's EHR in an authenticated and secure manner.

In some embodiments, the invention provides a method to create, access, and fuse EHRs. A sensor on the user generates a secret key. The sensor uses sensed physiological signals to hide the generated secret in the form of a fuzzy vault. The fuzzy vault is then transferred to the EHR server. The EHR server uses the generative model to synthesize timely physiological signal and uses it to unhide the secret from the vault. The secret is then used to securely transfer data from a sensor to the health record.

In some embodiments, the invention provides a method for authenticated access. The sensor on the user sends a sample of the physiological signal to the EHR server. The EHR server learns a model from the physiological signal sample. The server matches the learned model with the stored one. If there is a match access is granted.

In some embodiments, the invention provides a method for fusing EHRs based on a unique model of a physiological signal for each user. A sample of a first physiological signal is generated using a stored model. The system then obtains frequency domain features from the physiological signal and hides them in a fuzzy vault. A sample of a second physiological signal is also generated from a generative model and frequency domain features are obtained from the second signal. The system that generated the second signal then matches the features from the generative model with the features in the vault. If there is enough match among the two sets of features, then it is concluded that both the EHRs are of the same person and can be merged. In this way without any user involvement the two EHRs are authenticated to each other.

In one embodiment, the invention provides a method of encoding a data item string for secure transmission using a physiological signal. The data item string—for example, a 128-bit encryption key—is separated into a defined number of component segments. A polynomial equation is then constructed based on the data item string such that each component segment of the data item string is used as a different coefficient of the polynomial equation. A plurality of signal features are then identified from a physiological signal and a plurality of ordered pairs are created based on the plurality of identified signal features. In particular, the first element of each ordered pair corresponds to an index of a different one of the identified signal features and, when provided as an input to the constructed polynomial equation, produces the second element of the ordered pair as an output. Lastly, a data package is prepared for transmission including the plurality of ordered pairs.

In another embodiment, the invention provides a method of decoding a data item string from a received data package using a physiological signal. A plurality of signal features is identified and a plurality of data pairs is accessed from the data package. A subset of data pairs are identified from the data package as corresponding to one or more of the plurality of identified signal features—the remaining data pairs are rejected as "chaff points." Using LaGrangian interpolation, a polynomial equation is reconstructed such that, when the first element of each data pair of the subset of data pairs is provided as an input to the polynomial equation, the corresponding second element is calculated as the output of the polynomial equation. The data item string is reconstructed based on the coefficients of the reconstructed polynomial equation. In some embodiments, the data item string is reconstructed by appending the coefficients in order to form a larger, aggregated data string.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1A:
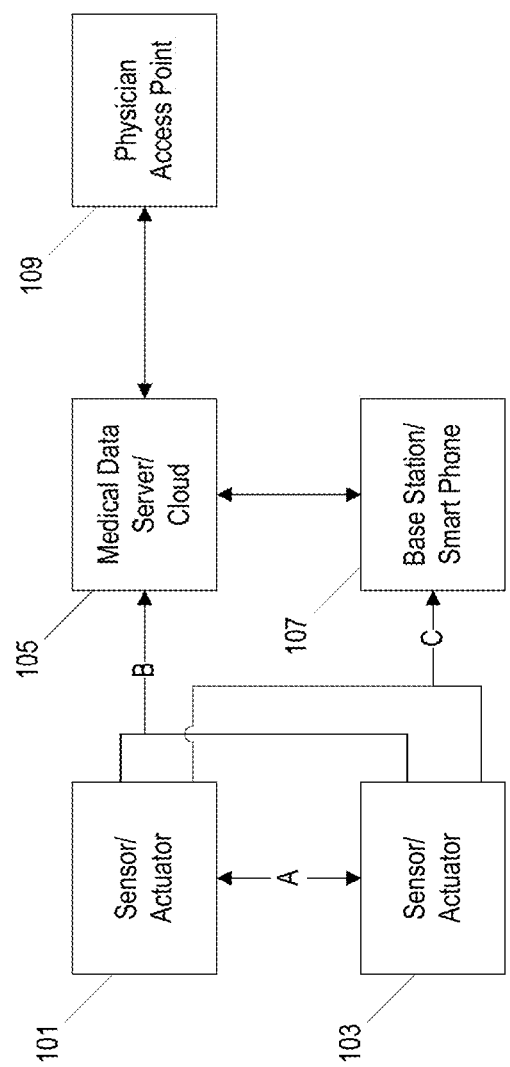
FIG. 1A is a block diagram of a communication network for generating, storing, and accessing medical records including information related to physiological signals detected by one or more sensors.

FIG. 1A illustrates one example of a communication network for medical systems including at least two sensors/actuators 101, 103, a medical data server (or cloud computing/storage environment) 105, a base station 107, and an access point 109 by which a physician or other medical professional can interact with the medical system communication network. The sensor/actuators 101, 103 are user-end devices that might, for example, measure a physiological signal of a patient (e.g., an electrocardiogram (ECG) system, a photoplethysmogram (PPG) system, or an electroencephalogram (EEG) system). The physiological signal data monitored and captured by the sensors 101, 103 may be used, for example, to trigger the actuation of another medical system or initial an alarm or may be stored on the medical data server 105 for later review and analysis by the patient and/or a medical professional (e.g., via physician access point 109). Alternatively, one or more of the user-end devices 101, 103 may include an actuator component such as, for example, an infusion pump to administer intervening measures in response (or based on) the physiological signal monitored by one or more connected sensor systems).

The medical data server 105 may be configured as a single server storage device or as a cloud-based storage mechanisms for storing, managing, and providing access to electronic health records (EHRs) for one or more patients. The server 105 may include, for example, one or more processors and one or more non-transitory memory storage units (e.g., hard-disk, flash, RAM, or ROM storage devices).

The base station 107 may be implemented as a dedicated device that is to be positioned near the patient in order to establish and maintain wired or wireless communication with one or more of the user-end sensor/actuator devices 101, 103. In some implementations, the base station is implemented as an application running on a smart phone or tablet computer that is to be carried by the patient.

The physician access point 109 is a device that is configured to access information that is stored on the medical data server/cloud 105 and, in some implementations, may be configured to control operations of one or more of the user-end sensor/actuator devices 101, 103 remotely and/or to send data (e.g., a message or an alarm signal) to the user base station 107 or to the sensor/actuator device 101, 103. In some implementations, the physician access point 109 is implemented as a personal computer device (e.g., a desktop, laptop, notebook, or tablet computer or a smart phone) configured to establish and manage wired or wireless communication with the medical data server 105, for example, through the Internet or another type of network. In such implementations, the physician access point 109 will include at least one processor and one or more non-transitory computer readable memories. The memory or memories store instructions that are executed by the processor to, among other things, provide communication and data processing functionality.

As described in further detail below, there are various different communication mechanisms that can be implemented either simultaneously or alternatively to facilitate communication between various components in the medical communication network illustrated in FIG. 1A. For example, one sensor/actuator device 101 may be configured to communicate directly with another sensor/actuator device 101 through wired or wireless communication protocol (e.g., Bluetooth) (communication path A). Alternatively, the base station 107 may be configured to facilitate communication between the two sensors/actuators 101, 103.

In order to allow for remote access of the medical data and to maintain an electronic health record (EHR) for the patient, the sensor/actuator devices 101, 103 may be configured to communicate with the medical data server 105. In some implementations, the sensor/actuator devices 101, 103 are configured to communicate with the medical data server 105 directly (i.e., communication path B). For example, the sensor/actuator devices 101, 103 may be equipped with IP communication mechanisms to communicate with the medical data server 105 directly through the Internet or may be equipped with a cellular communication module to establish communication with the medical data server 105 wirelessly over a cellular phone communication network.

In still other implementations, the sensor/actuator devices 101, 103 communicate with the medical data server 105 indirectly through the base station/smart phone 107 (i.e., communication path C). For example, the sensor/actuator devices 101, 103 can be configured to communicate with a smart phone 107 carried by the patient through a wireless communication mechanism such as Bluetooth, WiFi, or other near-field communication (NFC). The smart phone 107 will then establish communication with the medical data server 105 through the Internet or through a cellular communication network and transmit data to the medical data server 105 as necessary.

Figure 1B:
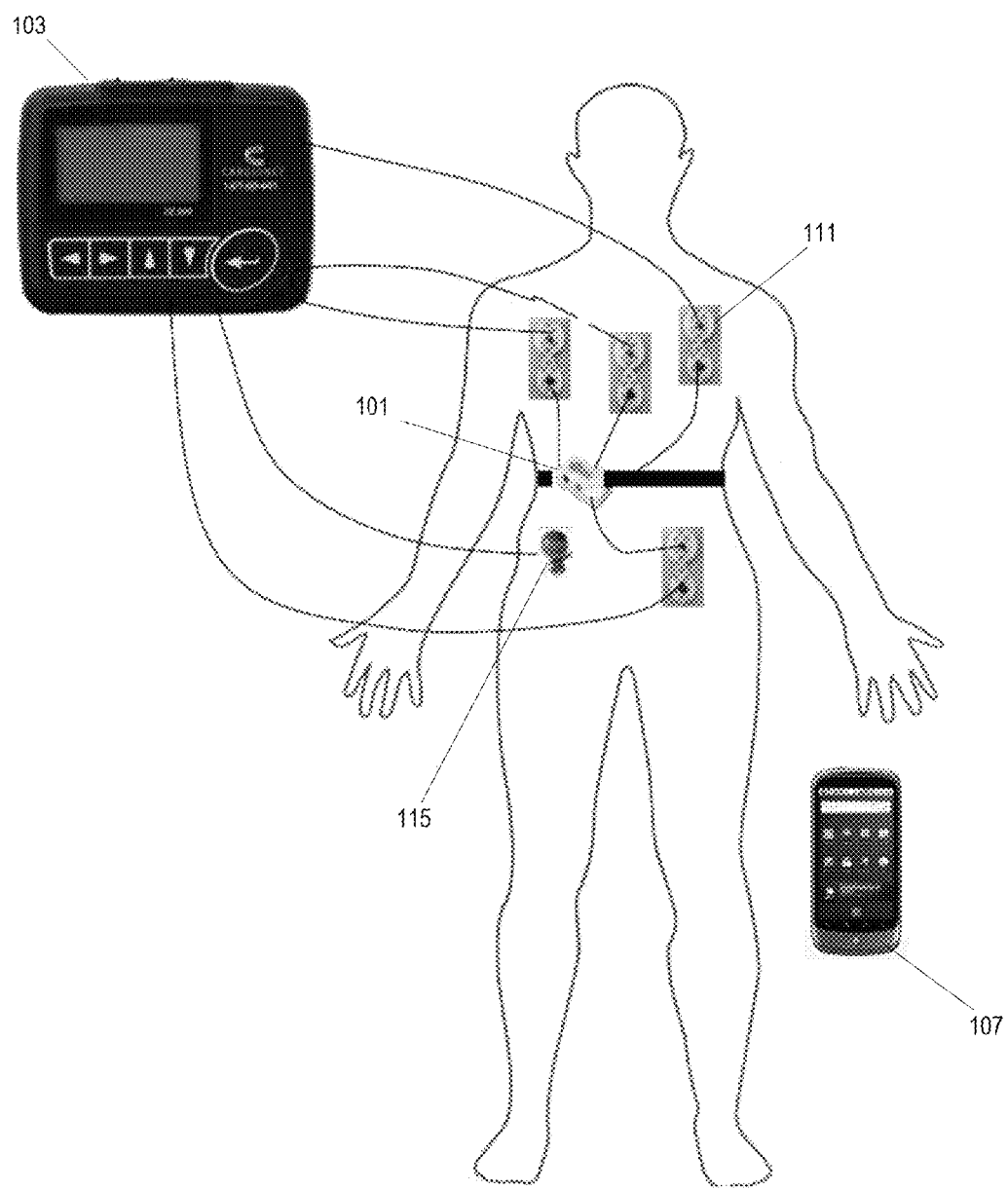
FIG. 1B is a schematic diagram of various components of a communication network such as illustrated in FIG. 1A for recording ECG signals.

FIG. 1B illustrates a specific example of one such medical communication network. In this example, the first sensor device 101 is an ECG monitoring system that is coupled by wire to a plurality of ECG leads 111 positioned on the body of a patient. A more advanced monitor system 103 (e.g., a "Holter monitor") is also coupled to each ECG electrode 111 and also to an AgCl sensor 115 positioned on the body of the patient. The patient carries a smart phone 107 running an application that allows the smart 107 to operate as a base station that performs various data processing/monitoring functions and also facilitates communication between the ECG monitor 101 and the Holter monitor 103.

In the system of FIG. 1B, it may be necessary for the ECG monitor 101 and the Holter monitor 103 to communicate with each other. Similarly, it may be necessary for the physiological data captured by the ECG monitor 101 and the Holter monitor 103 to be transmitted to a remote medical data server 105 for storage and/or later processing.

Figure 2:
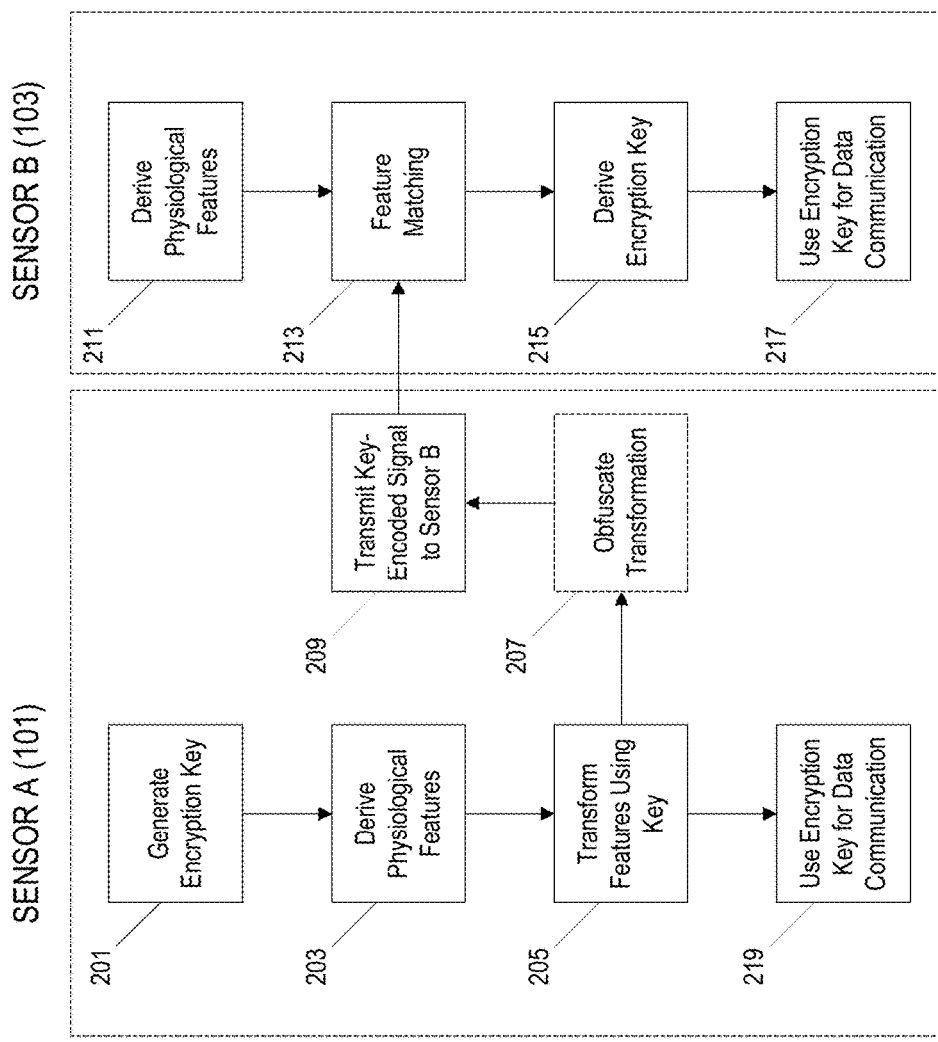
FIG. 2 is a flowchart of a method for distributing an encryption key encoded in a physiological signal for secure communication between two physiological sensor systems that each monitor a physiological signal of the same patient.

To provide for encrypted communication between the two sensor systems 101, 103 or between the smart phone 107 and a remote server (or cloud) storage system 105, an encryption key must be distributed to both devices. That encryption key will then be used to encrypt data communications. FIG. 2 illustrates one example of a method for securely distributing an encryption key from the first sensor system 101 to the second sensor 103 using the patient's own physiological signals to obscure the encryption key.

First, an encryption key is generated by the first sensor system 101 (step 201). This encryption key can be selected according to a variety of different key generation mechanisms including, for example, a random number generator. The first sensor system 101 then derives certain physiological features from a physiological signal monitored by the first sensor system 101 (step 203). For example, in the system of FIG. 1B, the ECG system 101 will monitor the patient's ECG signal for various features. The detected physiological features are then transformed based on the generated encryption key (step 205). In some implementations, the combined data set (i.e., generated based on both the physiological signal data and the encryption key) is further obfuscated, for example, by inserting further randomly generated "chaff points" as discussed in further detail below (step 207). The key-encoded physiological signal is then transmitted from the first sensor device 101 to the second sensor device 103 (step 209).

The second sensor 103 is also configured to monitor a physiological signal of the same patient. In some implementations, the two sensor systems 101, 103 are configured to monitor the same physiological signal. For example, in FIG. 1B, both the ECG system 101 and the Holter monitor 103 monitor ECG leads. Therefore, the second sensor 103 is able to use the same processing mechanism as the first sensor 101 (in step 203) to derive identifiable physiological features from the physiological signal (step 211). The second sensor system 103 performs feature matching between the two physiological signals (step 213) and, based on the matched features from the common physiological signal, is then able to derive the encryption key from the key-encoded signal (step 215). Once the encryption key is derived by the second sensor system 103, the encryption key can be used by the second sensor system and the first sensor system to provide for secure, encrypted communication between the two sensors systems (steps 217 and 219, respectively).

In other implementations, as discussed further below, the sensor systems may be configured to monitor different physiological signals; however, they can be configured to derive similar physiological features for each signal that establish a physiological signature of the patient that is common to both physiological signal and that can be used to unlock the encryption key from the key-encoded signal from the first sensor 101.

Furthermore, the physiological signal can be used as a vehicle to encode other "secret" data and, thereby, in some implementations, may itself be used as an encryption key. For example, in the method of FIG. 2, instead of generating an encryption key at step 201, the first sensor system 101 may generate or capture other data that is to be communicated to the other sensor system 103. For example, the first sensor system 101 may have calculated a heart rate for the patient based on the ECG signal or received other patient data through a user interface that is to be shared with the other communicative-coupled sensor device 103. The sensor system 101 will again derive physiological features from the monitored physiological signal (step 203) and transform the features using the "secret" data that is to be communicated to the other device (step 205). The "secret"-encoded signal is then transmitted to the second sensor system 103 where it is decoded (step 215) using a physiological signal monitored by the second sensor.

Although some of the other examples described below may specifically refer to using the same physiological signal to encode and decode data, it is to be understood that disparate physiological signal may also be utilized to derive a shared "physiological signature" data that is common to both signals. Furthermore, although examples below may specifically refer to encoding an encryption key in the physiological signal, such mechanism may be adapted to transmit other "secret" data between various systems such that the physiological signal itself serves as the encryption key.

In addition to facilitating secure communication, the physiological signal encryption mechanism may be used to confirm whether a new incoming electronic health record (EHR) should be included as part of the electronic medical record for a specific person. Furthermore, the physiological signal feature matching may be used to aggregate and compile previously stored electronic medical records during system reorganization. For example, this technique may be used to facilitate updating and reorganizing data records associated with a single patient from various sources through a cloud-computing environment.

Furthermore, in this era of wearable tech devices and smart phone proliferation, a user has a plethora of non-clinical devices that record important information on behavior and physiology that can be useful in managing health risks. Such data for a given user is very valuable and can be used, for example, in two ways: (a) the data can be processed to provided behavioral feedback to the user through a smartphone application and (b) care providers can be granted access to this data as needed during both normal office-visits and during emergencies.

Figure 3:
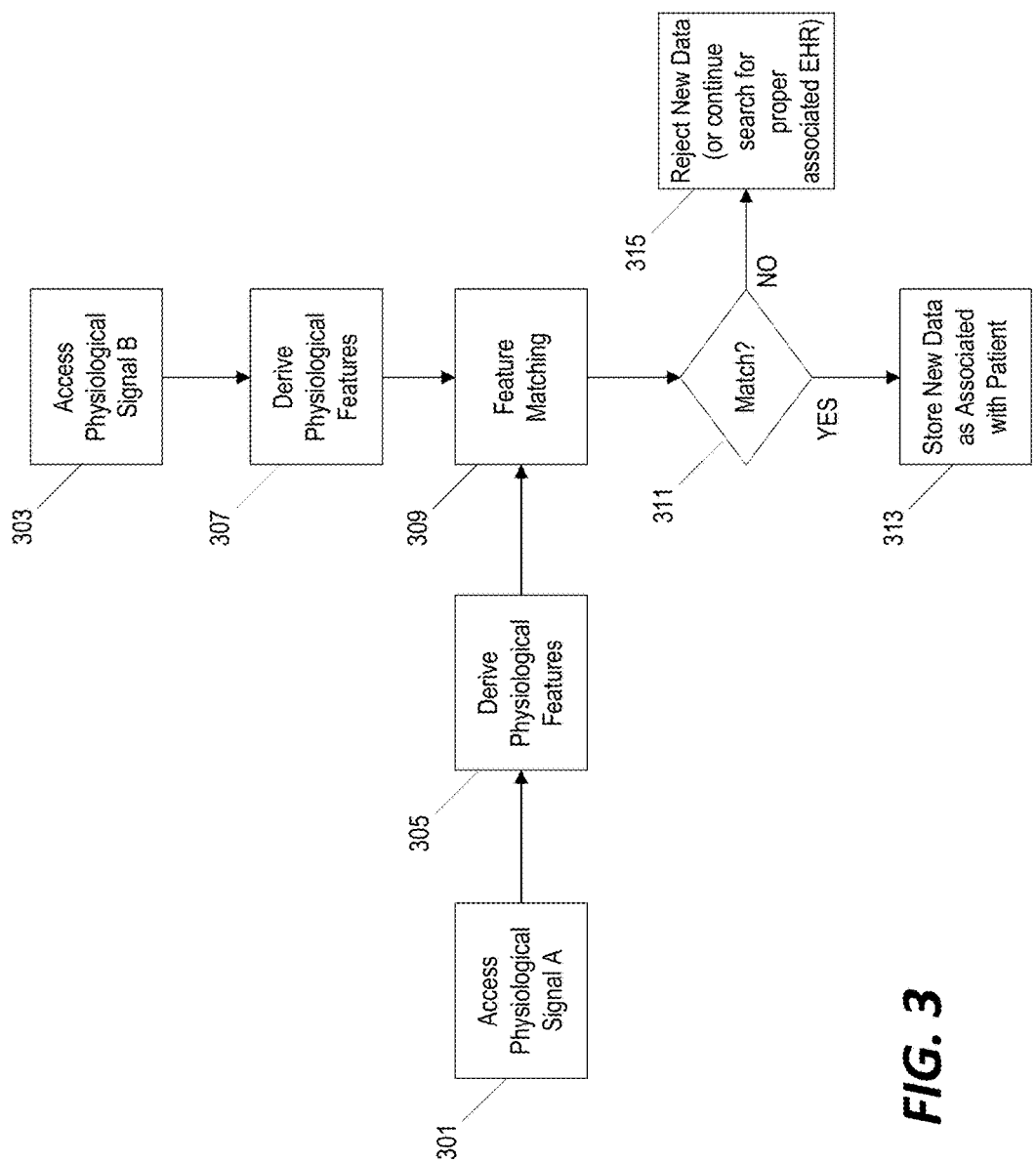
FIG. 3 is a flowchart of a method for associating new medical information with an existing electronic health record of a patient based on a comparison between two physiological signals.

FIG. 3 illustrates a method for reconciling electronic health records and for confirming that the electronic records indeed match for a given patient. This method may be implemented by the remote server 105, the physician access point, or another device coupled to the communication network. The system access a first physiological signal—Signal A—for the patient (step 301) and a second physiological signal (step 303). In some implementations, Signal A is a signal that has already been confirmed as being associated with a specific patient's electronic record and Signal B is either a new incoming physiological signal or another previously stored physiological signal that has not yet been matched with the aggregated health record for the patient. In other implementations, Signal A and Signal B are both previously stored physiological signals and the system is attempting to match stored records to build a new aggregated medical record for the specific patient.

The system derives physiological features from Signal A and Signal B (steps 305 and 307, respectively) and performs feature matching on the two signals (step 309). If the system confirms that the two signals match and indeed belong to the same patient (step 311), the system stores the signals as electronic health records associated with the same patient (step 313). However, if the signals do not match, the system either rejects the new signal or continues searching for a proper association with another patient's EHR (step 315).

In the methods discussed above, secure encryption and data matching using a physiological signal is performed where both the transmitting device and the receiving device have access to physiological signal for a single patient. For example, in the method of FIG. 2, a signal is being sent from a first sensor system 101 that measures a physiological signal of the patient to another sensor system 103 that also measures the physiological signal of the patient. However, when establishing secure communication with a remote server (or cloud) 105, the recipient system will not have access to a real-time physiological signal for the patient.

Figure 4:
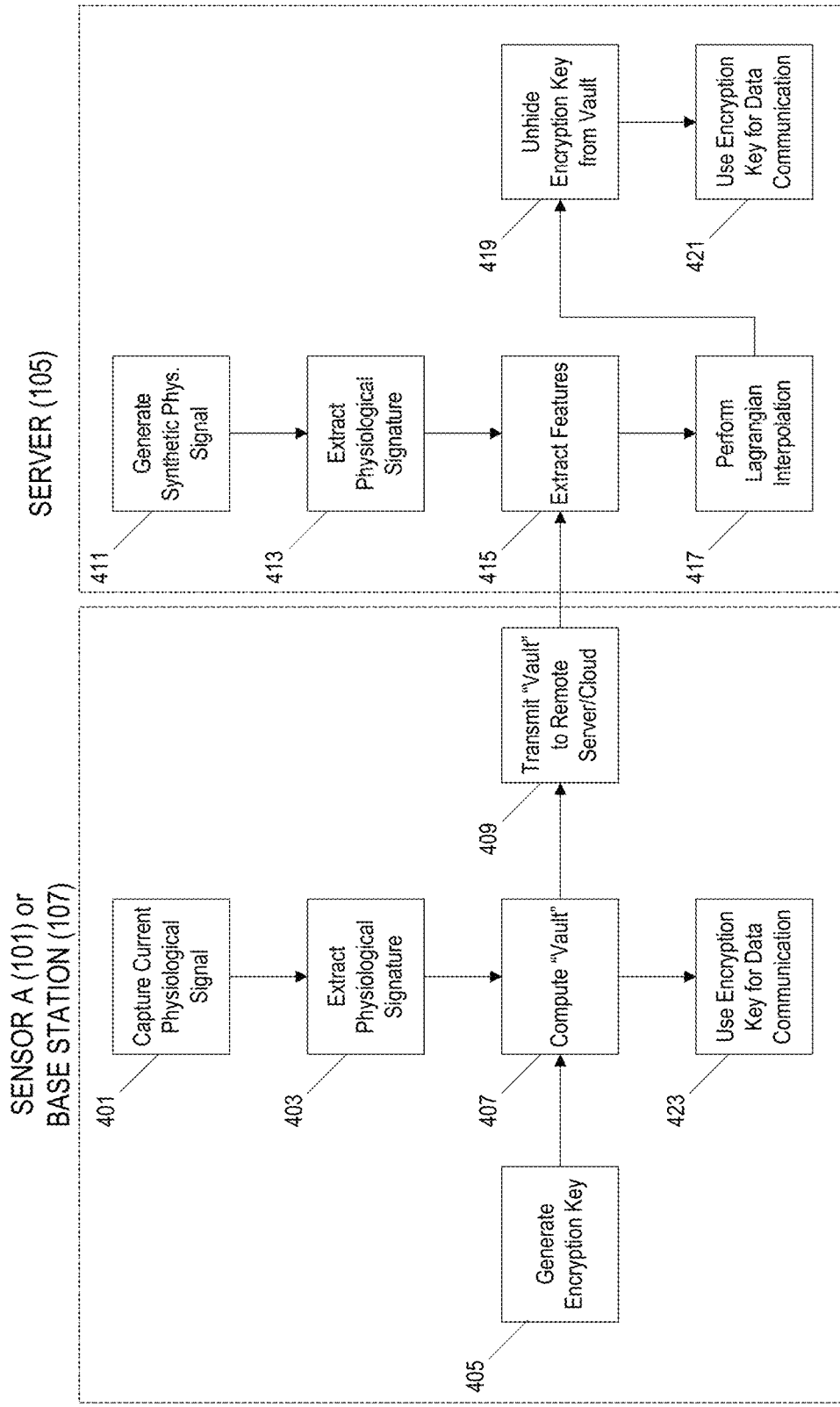
FIG. 4 is a flowchart of a method for distributing an encryption key encoded in a physiological signal for secure communication between a sensor system and a remote server or cloud system.

FIG. 4 illustrates a method for establishing secured, encrypted communication between one system that has access to a physiological signal for a patient (e.g., sensor system 101, which measures the signal, or base station 107, which receives the physiological signal from sensor system 101) and a second system that does not have live access to any physiological signal for the patient (e.g., a remote server 105). Like in the earlier example, the user-end system captures a live physiological signal for the patient (step 401) and extracts a physiological signature from the signal (step 403). An encryption key (or other "secret" data) is generated (step 405) and combined with the physiological signature data to compute a data "vault" (step 407). The data "vault" is then transmitted from the user-side device to the other system (e.g., server 105) (step 409).

Instead of using a live physiological signal for the patient, the second system (e.g., server 105) generates a synthetic physiological signal for the specific patient using, for example, a previously stored and tuned model for the patient signal (step 411). The second system extracts the physiological signal from the synthesized signal (step 413), extracts common features from the received data "vault" (step 415), and performs an interpolation/transformation (such as, for example, a Lagrangian interpolation) (step 417) to unhide the encryption key (or other "secret" data) from the received "vault" (step 419). Once the encryption key is derived, it is used to facilitate secure encrypted communication between the user-end device (e.g., sensor 101 or base station 107) and the remote device (e.g., server 105) (steps 421 and 423, respectively).

Figure 5A:
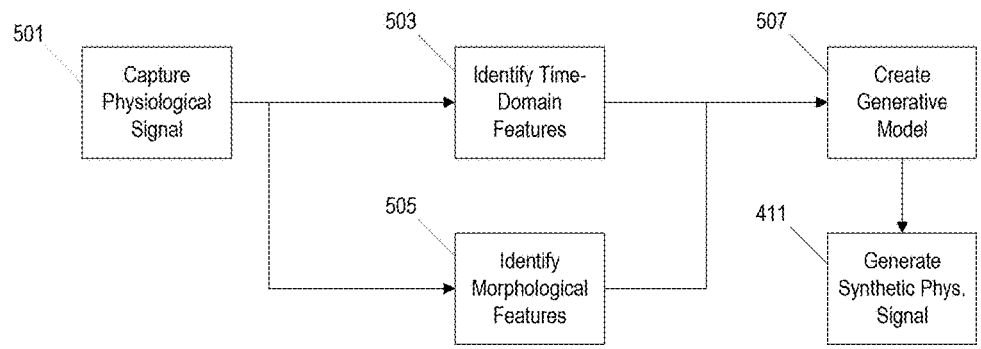
FIG. 5A is a method of initializing the remote server to decode an encryption key encoded in physiological signal data received from a sensor system using a synthesized physiological signal.

FIG. 5A illustrates an example of one mechanism for deriving a physiological signature and for creating a generative model to be used by the remote system in the method of FIG. 4 to generate a synthetic physiological signal. First, the system captures or receives a physiological signal (step 501). The system then identifies time-domain features of the physiological signal (step 503) and morphological features of the same physiological signal (step 505). The separate time-domain and morphological features are then used to create a generative model (step 507) that is stored on the remote system and used to generate the synthetic physiological signal (step 411).

Figure 5B:
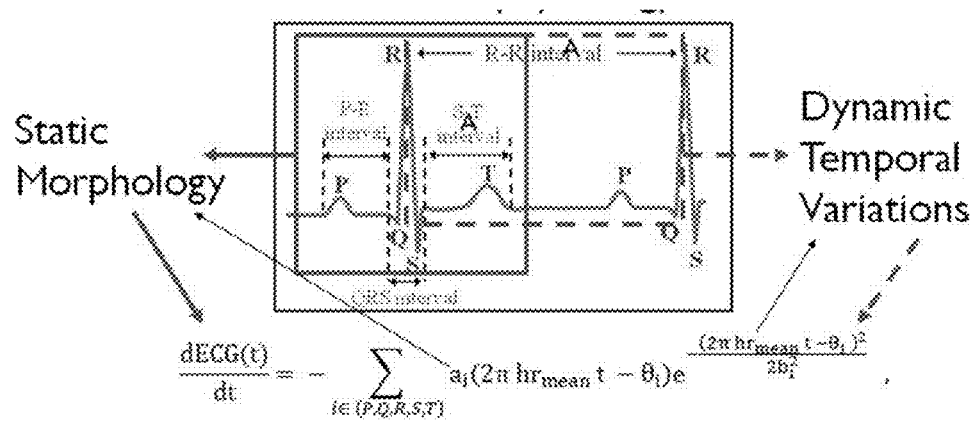
FIG. 5B is a graph illustrating the static morphology and temporal variations used to derive a physiological signature of an ECG signal.

FIG. 5B illustrates an example of a generative mathematical model for an ECG signal. The illustrated ECG signal includes the characteristic QRS complex, P, and T features of an ECG signal. The dynamic temporal variations (e.g., the periodic R-R interval) might change based on the patient's current activity or health level. These temporal variations (i.e., time-domain features) are represented mathematically by the right side of the mathematical expression in FIG. 5B. The morphological features relate more to the general shape of the physiological signal (i.e., the signal morphology). It has been observed that, for ECG and PPG signals in particular, the morphology parameters changes very slowly over the lifetime of a person and, therefore, may be utilized as a reliable physiological signature over time. The morphological component is represented by the left side of the mathematical expression in FIG. 5B and can be determined mathematically. Specific mechanisms for deriving morphological features and physiological signatures are discussed in further detail below.

Figure 6A:
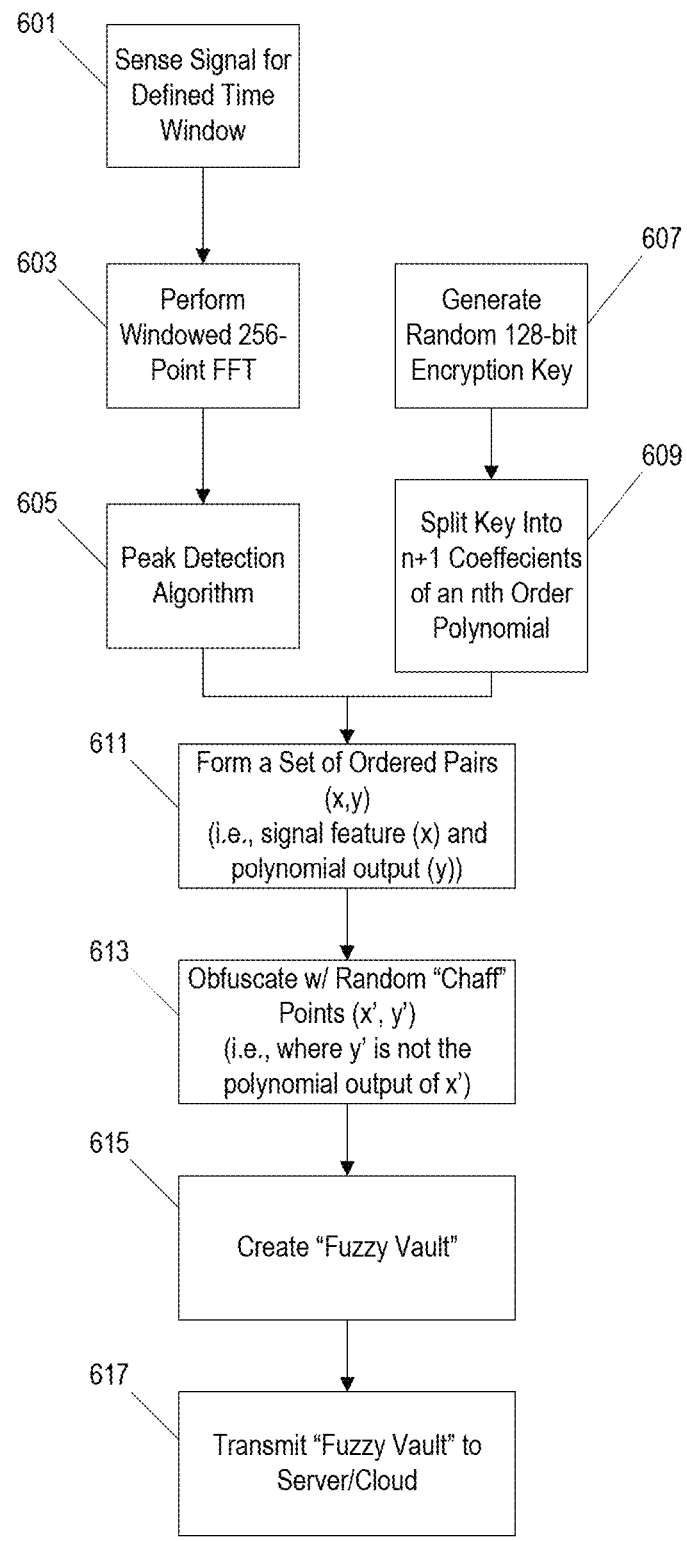
FIG. 6A is a method of encoding an encryption key in a monitored physiological signal.

FIG. 6A illustrates a specific mechanism for generating an obfuscated and encrypted data "vault" for encrypted communication between devices/systems. The sender system monitors and isolates a physiological signal for a defined time window (e.g., 30 seconds) (step 601). The sender system then performs a windowed 256-point fast Fourier transform (FFT) on the signal snippet (step 603) and runs a peak detection algorithm on the FFT output signal (step 605). The detected peaks are each identified by a time index and the corresponding magnitude value and then concatenated to form a 16-bit "feature" component. The sender system also generates a random 128-bit encryption key (step 607) and splits the key into n+1 values that will serve as coefficients of an nth order polynomial (step 609).

The generated polynomial is then used to create an ordered pair for each "feature" component identified in step 605 (step 611). Each pair is of the form (x,y) where x is the identified signal feature and y is the output of the polynomial when x is used as the input parameter of the polynomial. The data set is then obfuscated by generated a plurality of random "chaff point" pairs (x', y') (step 613). The chaff point numbers are generated at random with the rule that the y' cannot be equal to the polynomial output of x'. The ordered pairs and the chaff point points are combined into a data package to form a "fuzzy vault" (step 615) and are transmitted to a "receiver system" (step 617).

Figure 6B:
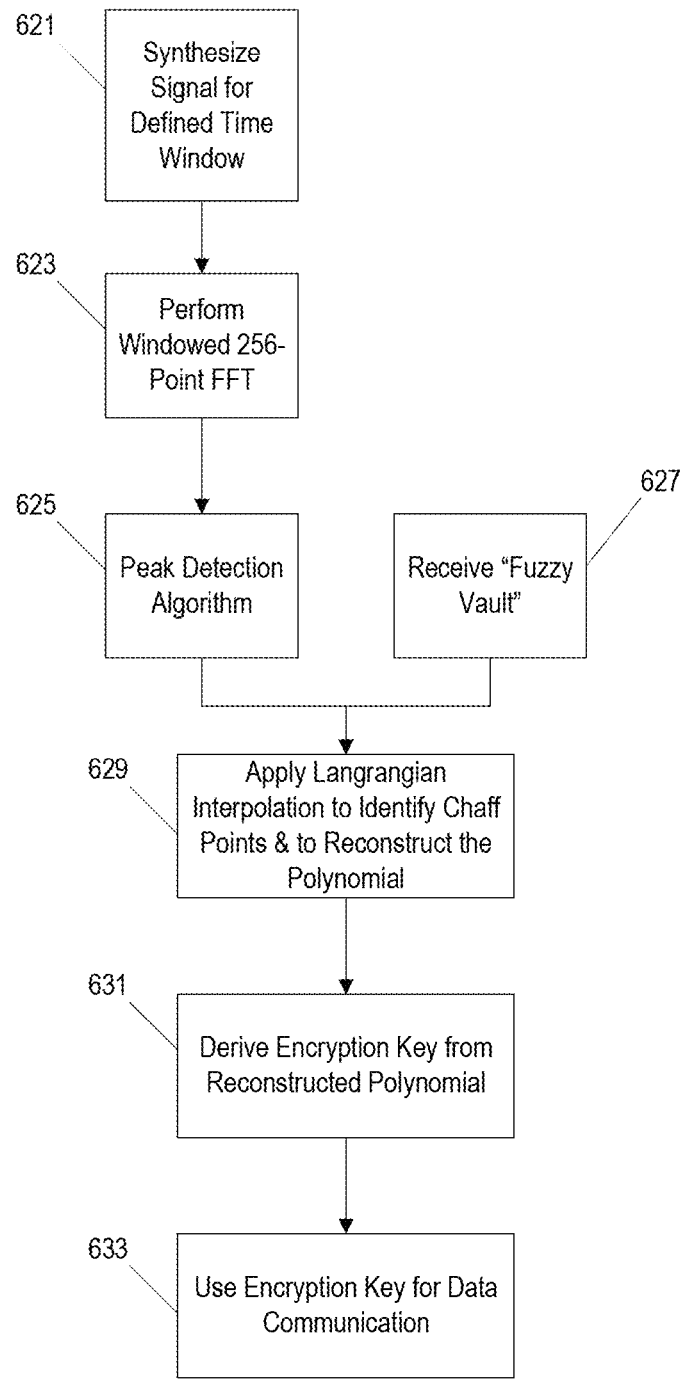
FIG. 6B is a method of decoding the encryption key from the method of FIG. 6A using a synthesized physiological signal.

FIG. 6B illustrates a method for decrypting the "fuzzy vault" received by the receiver system to derive the 128-bit encryption key encoded therein. First, the receiver system generates a synthesized physiological signal based on a stored, previously-initialized generative signal model for the patient (step 621). The duration of the synthesized physiological signal is again limited to the same time window as used by the sender device during the encryption process. The receiver system performs a windowed 256-point FFT on the synthesized signal snippet (step 623) and applies the same peak detection algorithm on the FFT output signal (step 625). Each detected peak from the synthesized signal is identified by a time index and the corresponding magnitude value from the synthesized signal and concatenated to form a 16-bit "feature" component.

After the receiver system receives the "fuzzy vault" from the sender system (step 627), the receiver system applies Langrangian interpolation to reconstruct the polynomial and, in the process, identify and remove the chaff points from the "fuzzy vault" (step 629). As a result, the receiver system identifies an nth order polynomial that fits a large number of the pairs in the "fuzzy vault" (i.e., the ordered pairs (x, y)) and does not fit a number of other pairs (i.e., the "chaff pairs" (x', y')). The coefficients of the reconstructed nth order polynomial are combined to derive the encryption key (step 631). The derived encryption key is then used for subsequent secure, encrypted communication between the sender system and the receiver system (step 633).

Again, although the example of FIGS. 6A and 6B specifically refer to encoding an encryption key into a "fuzzy vault," the same encoding and decoding mechanism can be used to securely transmit other "secret" information from a sender system to a receiver system. For example, other information from the sender system can be represented as a 128-bit data string, broken into n+1 polynomial coefficients, and the resulting polynomial used to create ordered pairs for each of a plurality of identified signal features. Instead of using the method of FIG. 6B to decode a 128-bit encryption key, the receiver system would use the same process to decode the other "secret" information that was used to create the polynomial and the generated set of ordered pairs.

Figure 7A:
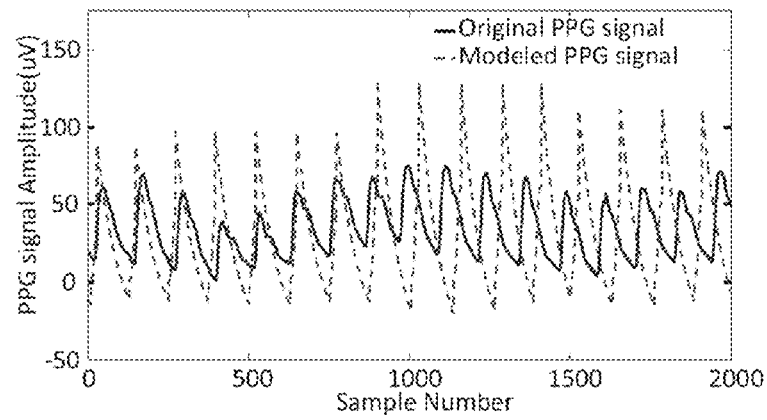
FIG. 7A is a graph of a photoplethysmogram (PPG) signal measured by a sensor system compared to a synthesized PPG signal generated based on a generative signal model.
Figure 7B:
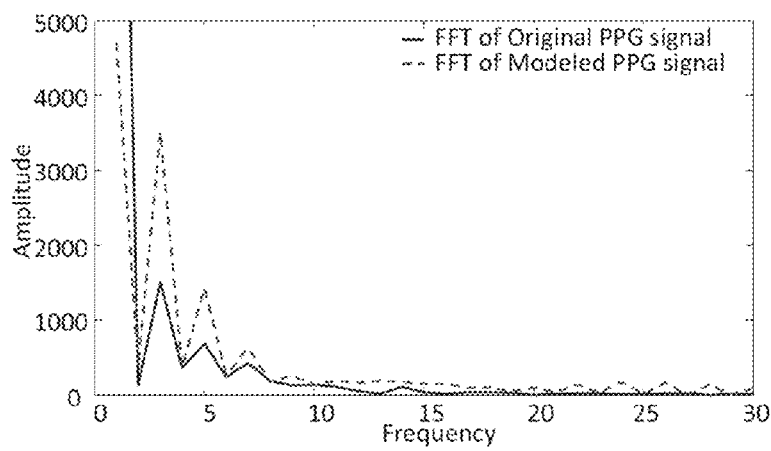
FIG. 7B is a graph of the measured PPG signal and the synthesized PPG signal of FIG. 7A transformed to the frequency domain using a Fourier transform.
Figure 7C:
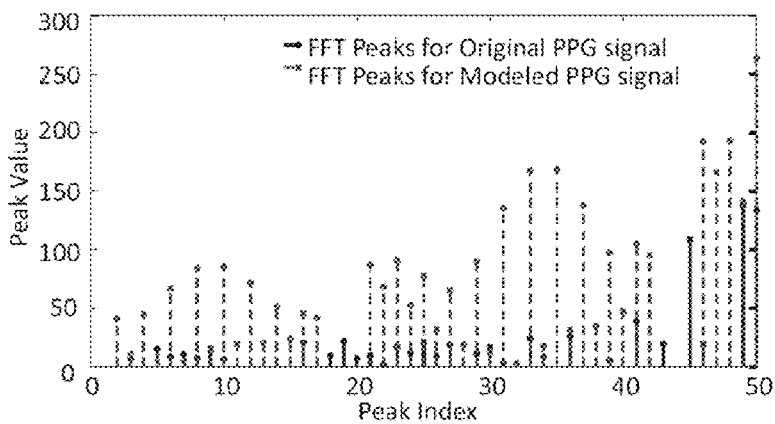
FIG. 7C is a graph of identified peak features of the FFT of the measured signal and the FFT of the synthesized signal of FIG. 7B that are used for encoding the encryption key in the method of FIG. 6A and for decoding the encryption key in the method of FIG. 6B.

FIGS. 7A, 7B, and 7C illustrate an example of PPG signal data (both live captured and synthesized) used to encode and decode the encryption key according to the methods of FIGS. 6A and 6B and further illustrate the morphological signature present in both the live captured physiological signal and the synthesized physiological signal. FIG. 7A illustrated a PPG signal for a patient based on 2000 captured sample points over a defined time window (i.e., the solid line) and a modeled PPG signal for the same patient over the same defined time window (i.e., the dotted line). As shown in FIG. 7A, the exact amplitude and frequency (i.e., temporal features) of the modeled PPG signal do not match the actual measured patient signal. However, after the FFT is performed on both the live data signal and the modeled signal, the peak frequencies to begin to align as shown in FIG. 7B. When the peak detection routine is performed on the FFT output signal, multiple peak indexes are identified that are common to both the measured PPG signal and the modeled PPG signal. These common peak indexes serve as the physiological signature that is used to encode and decode the encryption key in the "fuzzy vault."

Figure 8A:
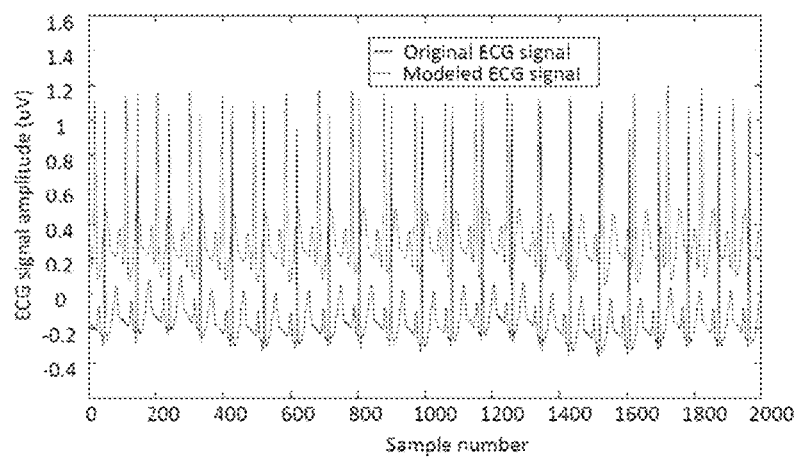
FIG. 8A is a graph of an electrocardiogram (ECG) signal measured by a sensor system compared to a synthesized ECG signal generated based on a generative signal model.
Figure 8B:
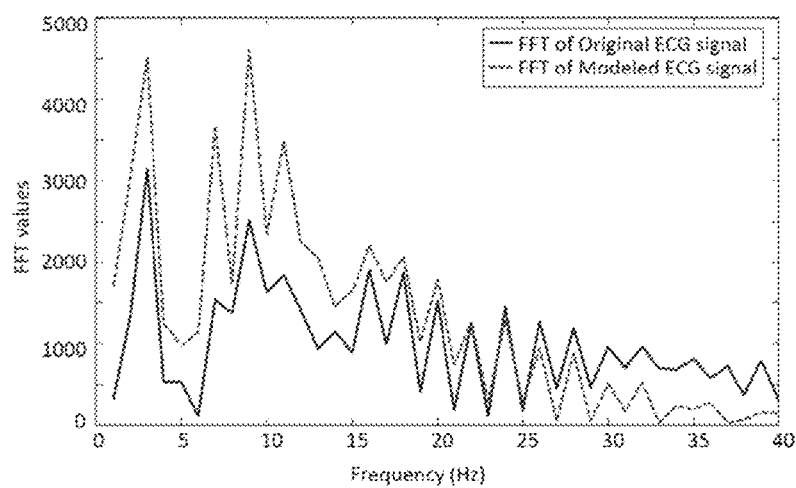
FIG. 8B is a graph of the measured ECG signal and the synthesized ECG signal of FIG. 8A transformed to the frequency domain using a Fourier transform.
Figure 8C:
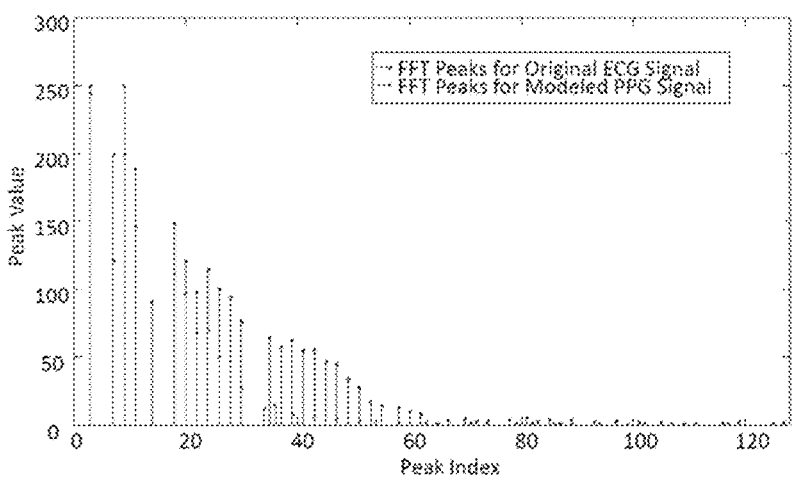
FIG. 8C is a graph of identified peak features of the FFT of the measured signal and the FFT of the synthesized signal of FIG. 8B that are used for encoding the encryption key in the method of FIG. 7A and for decoding the encryption key in the method of FIG. 6B.

Similarly, FIGS. 8A, 8B, and 8C illustrate an example of ECG signal data used to encode and decode an encryption key (or other "secret" data) in a "fuzzy vault." Again, as shown in FIG. 8A, the temporal features of the modeled signal do not match those of the actual measured ECG signal. However, as shown in FIG. 8B, when an FFT is performed on both signals, the aligned peaks are identified and, as shown in FIG. 8C, these common peak indexes are uniform enough to serve as a common physiological signature used to encode and decode the encryption key. Furthermore, any peak indexes from one signal that are not also present in the other signal would be identified as "chaff points" in the fuzzy vault and would not affect the reconstruction of the polynomial encoding the encryption key.

As discussed above, some implementations utilize the same physiological signal for both encoding and decoding—for example, a measured ECG signal is used to generate the "fuzzy vault" and a synthesized ECG signal is used to derive the encrypted data from the "fuzzy vault." However, in some other implementations, a received data vault may be decoded using a signal that is different than the one used to construct the vault. In such implementations, two cases arise: (a) a pair of coherent signals that are generated by the same underlying physiological process of the body (e.g., an ECG signal and a PPG signal that are both related to the cardiac process) and (b) non-coherent signals that are generated based on totally different physiological processes of the body (e.g., an ECG signal based on cardiac process and an EEG signal based on neural activity).

Figure 9:
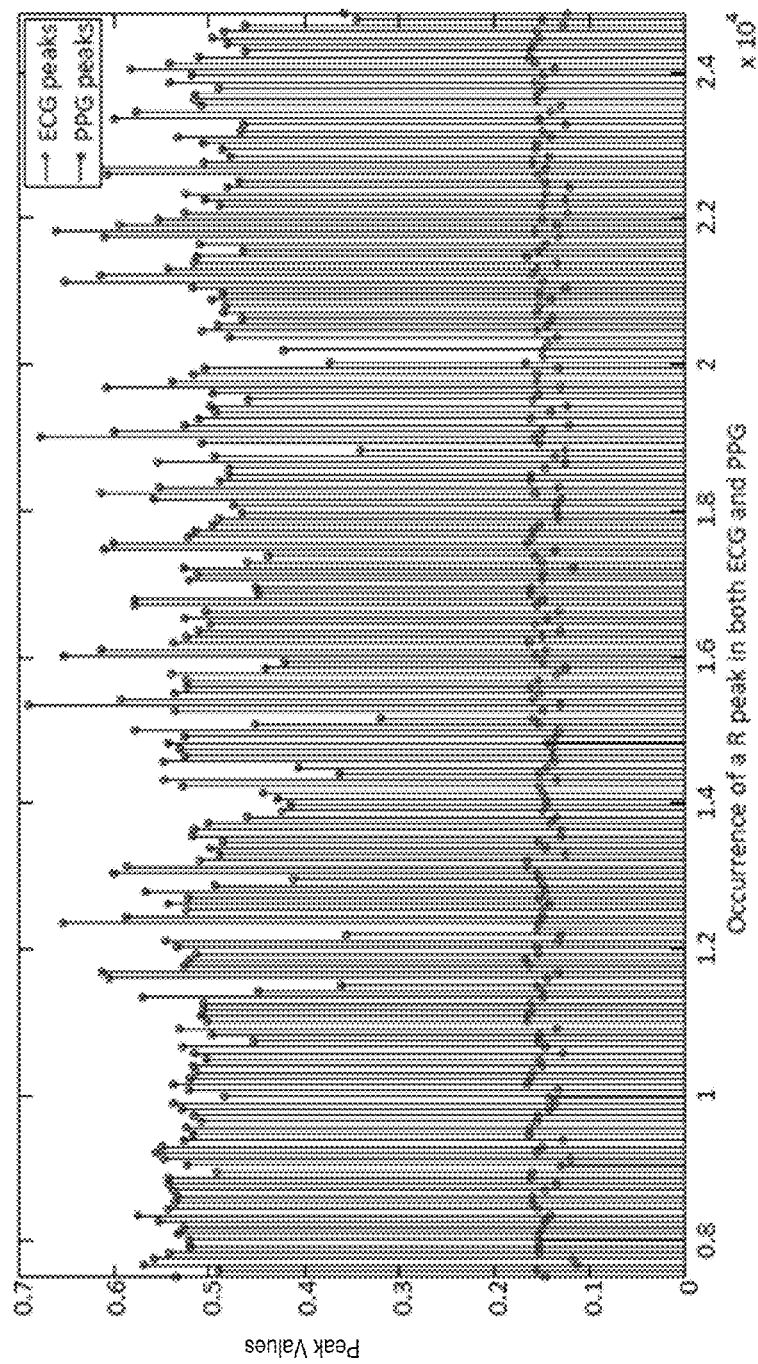
FIG. 9 is graph comparing the temporal properties (e.g., FFT signal peaks) of an ECG signal and a PPG signal.

For coherent signals, the system may be configured based on the fact that there will be a considerable amount of correlation among the temporal parameters of two signals generated by the same underlying physiological process. Although the morphology of the two signals may be very different, the temporal properties such as average heart rate, standard deviation, etc. reveal a close match between the two signals. Furthermore, some there may be morphological equivalence between two coherent signals—for example, the position of the R-beat in an ECG will coincide with a peak of a corresponding PPG signal. FIG. 9 illustrates this equivalence by showing the commonality of the R peak in both the ECG and PPG signals.

For this example, signal $S_A$ and signal $S_B$ have common temporal parameters $f_{AB}$ because they are coherent. Further, $G_A$ represents the generative model for signal $S_A$ and $m_A$ represents the morphological properties for signal $S_A$ that device B possess in a pre-deployed fashion (i.e., due to earlier initialization such as shown in FIG. 5A). Device A generates a secret session key k and uses the mechanism described above to hide the key using frequency-domain features derived from $S_A$ and sends the generated data vault to device B. Device B computes $f_{AB}$ based on its sensed signal $S_B$ and then uses $m_A$ and the time domain parameters $f_{AB}$ obtained from $S_B$ to generate the synthetic signal $S'_A$ from its generative model $G_A(f_{AB}, m_A)$. Device B then derives frequency-domain features from $S'_A$ and executes the method of FIG. 6B to unhide the key k. In order to perform this method as described above for coherent, but different, signals, the second device B must possess both the generative model and the morphological parameters of signal $S_A$. These can be pre-deployed during the initialization process of FIG. 5A.

Figure 10:
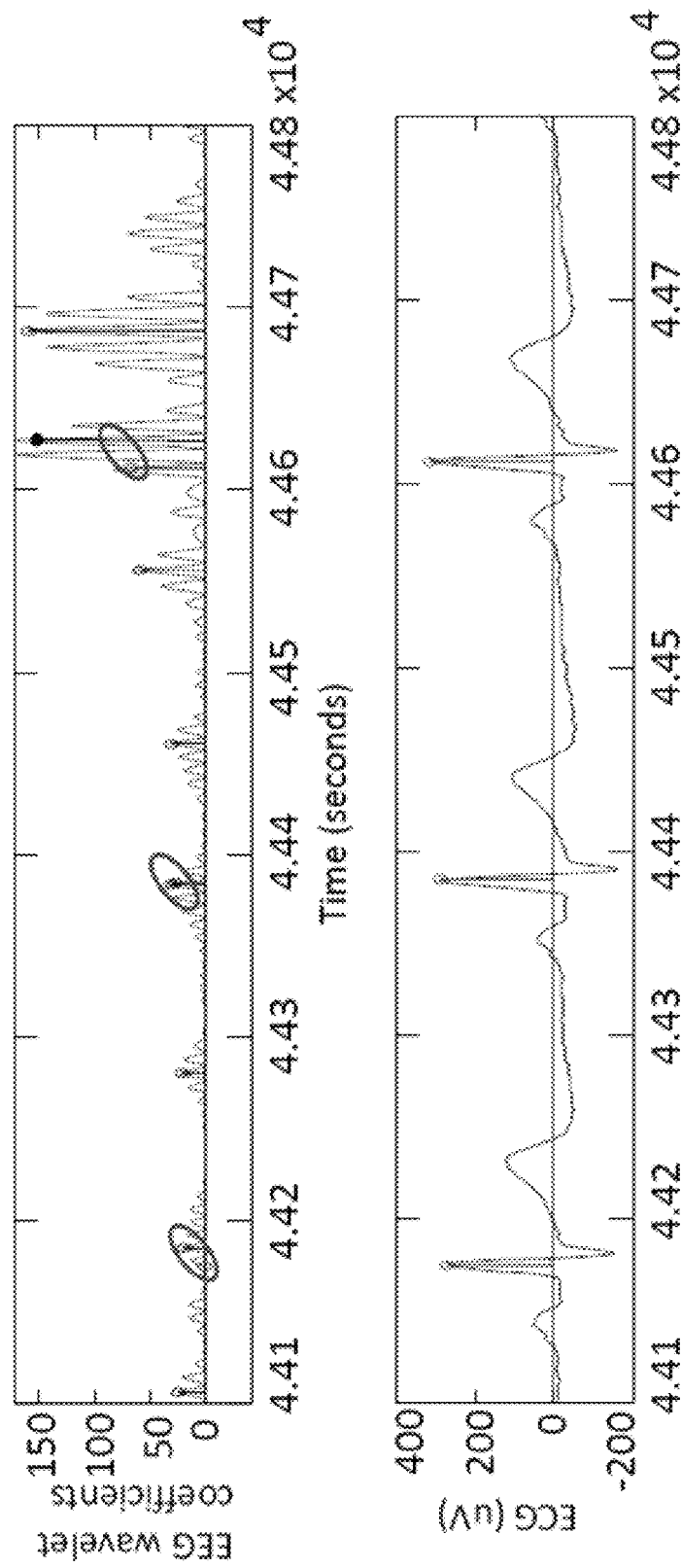
FIG. 10 is a graph comparing identified signal peaks from ECG signal data and identified signal peaks from EEG signal data.

Use of physiological signal encoding for non-coherent signals may be based on the hypothesis that coupling provided by the human body between different physiological processes ensures that some signature of signal $S_A$ is visible on a signal $S_B$ even if $S_A$ and $S_B$ are not produced from the same physiological process. Therefore, the encoding/decoding process for non-coherent signals as the processes described above for coherent signals except that $f_{AB}$ is now derived from a signal $S_B$ that is not coherent with $S_A$. As illustrated in FIG. 10, there is considerable coupling between ECG signal (based on heart function) and EEF signal (based on brain function). In particular, the R-peaks of the ECG signal can be obtained from the EEG signal for the user by implementing signal processing techniques. The time domain parameters of the generative model of the ECG can then be derived from these R peaks and can be used in conjunction with the morphology parameters of the ECG to perform the encoding/decoding processes such as described above.

In one specific implementation, an ECG signal can be extracted from and EEF signal using Continuous Wavelet Transform (CWT). CWT derives information about the available frequencies in the signal at a particular time. CWT uses a basic signal function which is scaled according to the frequency and time shift allowing specific shape properties of the signal to be analyzed. For example, CWT for a signal x(t) may be expressed as:

$$x(t) = \frac{1}{\sqrt{(a)}} * \int_{-\infty}^{\infty} x(t)\varphi^*\left(\frac{t-b}{a}\right) dt$$

where a>0 is a scaling parameter, b is a shift parameter, and $\varphi^*$ is a wavelet function. The scale parameter a is used to denote how much the wavelet is stretched or compressed—the smaller the value of a, the more compressed the wavelet. For each R-peak in the ECG signal, there is a corresponding disturbance in the wavelet transform of the EEG signal as shown in FIG. 10. The scale parameters from the wavelet transform of the EEG signal exhibit this disturbance with the maximum magnitude.

With accurate signal processing techniques, the time values of each disturbance can be extracts and, thereby, identify the position of the R peaks in the ECG signal. These temporal parameters can then be used by a generative model to generate a synthetic ECG signal for decoding a received data vault according to the method of FIG. 6B.

Lastly, it is noted that, although specific examples described above focus on using physiological signals for secured and, sometimes, encrypted communication of medical information between multiple medical devices and systems, the physiological-signal-based encoding and decode mechanisms described above may be used in environments other than health record management. In fact, physiological-signal-based encoding might be implemented in any environment that has access to physiological signal from a user. For example, a user logging into a computer at work might provide an ECG signal. The ECG signal might then be used to encode a random encryption key (or even a user specified password) to create a "fuzzy vault." The fuzzy vault would then be decoded by the remote computer system to determine whether to provide access to the user and to encryption data in subsequent transactions. The mechanism might be similarly implemented to provide access to banking information or physical access as part of a high-security building access system.

Thus, the invention provides, among other things, a system and method for secure communication between a sender system and a receiver system by encoding secret data in a physiological signal. Various features and advantages of the invention are set forth in the following claims.

What is claimed is:

1. A method of decoding a data item string from a receiving data package using a physiological signal, the method comprising:
  identifying a plurality of signal features from a physiological signal;
  accessing a plurality of data pairs from the data package;
  identifying a subset of data pairs from the plurality of data pairs from the data package that correspond to one or more of the plurality of identified signal features from the physiological signal;

reconstructing a polynomial equation based on the subset of data pairs such that a second element in each data pair of the subset of data pairs corresponds to an output of the reconstructed polynomial equation when a corresponding first element in the data pair is used as an input to the reconstructed polynomial equation; and deriving the data item string based on the coefficients of the reconstructed polynomial equation, wherein the physiological signal is an ECG signal, and wherein identifying the plurality of signal features includes identifying an R-peak corresponding to each cardiac rhythm cycle.

2. The method of claim 1, further comprising detecting the physiological signal from a body of a user through a sensor system.

3. The method of claim 1, further comprising accessing a previously-stored physiological signal associated with a specific user from a non-transitory computer-readable memory, and wherein identifying the plurality of signal features from the physiological signal includes identifying a plurality of signal features from the accessed, previously-stored physiological signal associated with the specific user.

4. The method of claim 1, further comprising:
generating a synthesized physiological signal for a specific user based on a generative signal model initialized for the specific user, and
wherein identifying the plurality of signal features from the physiological signal includes identifying a plurality of signal features from the synthesized physiological signal.

5. The method of claim 4, wherein the act of generating a synthesized physiological signal for a specific user is performed by an electronic health records storage system.

6. The method of claim 5, further comprising:
receiving, by the electronic health records storage system, a subsequent data package;
using the data item string to decode data from the subsequent data package; and
storing the decoded data from the subsequent data package as an electronic health record on a non-transitory computer-readable memory of the electronic health records storage system.

7. The method of claim 1, further comprising:
identifying a plurality of chaff points from the plurality of data pairs from the data package, wherein the plurality of chaff points include points that do not correspond to any of the identified signal features from the physiological signal; and
disregarding the identified chaff points while reconstructing the polynomial equation.

8. The method of claim 1, wherein reconstructing the polynomial equation based on the subset of data pairs includes reconstructing the polynomial equation using LaGrangian interpolation.

9. The method of claim 1, wherein identifying the plurality of signal features includes performing a Fourier transformation on a physiological signal sample of a defined duration and identifying a plurality of peaks in the Fourier-transformed physiological signal.

10. The method of claim 1, further comprising receiving the data package from a PPG sensor, wherein the data points of the data package correspond to R-peaks detected in a PPG sensor signal.

11. The method of claim 1, further comprising receiving the data package from an EEG sensor system, wherein the data points of the data package correspond to components in the EEG signal corresponding to the R-peaks.

12. A method of decoding a data item string from a receiving data package using a physiological signal, the method comprising:
identifying a plurality of signal features from a physiological signal;
accessing a plurality of data pairs from the data package;
identifying a subset of data pairs from the plurality of data pairs from the data package that correspond to one or more of the plurality of identified signal features from the physiological signal;
reconstructing a polynomial equation based on the subset of data pairs such that a second element in each data pair of the subset of data pairs corresponds to an output of the reconstructed polynomial equation when a corresponding first element in the data pair is used as an input to the reconstructed polynomial equation; and
deriving the data item string based on the coefficients of the reconstructed polynomial equation
wherein the physiological signal is an EEG signal and further comprising:
detecting elements in the EEG signal that correspond temporally to an R-peak in an ECG signal;
generating a synthesized ECG signal based on the EEG signal; and
receiving the data package from an ECG sensor system, wherein identifying the plurality of signal features includes performing a Fourier transformation on the synthesized ECG signal sample of a defined duration and identifying a plurality of peaks in the Fourier-transformed synthesized ECG signal, and
wherein the data points of the data package correspond to a plurality of peaks identified in a Fourier-transformed ECG signal detected by the ECG sensor system.

13. The method of claim 12, further comprising accessing a previously-stored physiological signal associated with a specific user from a non-transitory computer-readable memory, and wherein identifying the plurality of signal features from the physiological signal includes identifying a plurality of signal features from the accessed, previously-stored physiological signal associated with the specific user.

14. The method of claim 12, further comprising:
generating a synthesized physiological signal for a specific user based on a generative signal model initialized for the specific user, and
wherein identifying the plurality of signal features from the physiological signal includes identifying a plurality of signal features from the synthesized physiological signal.

15. The method of claim 14, wherein the act of generating a synthesized physiological signal for a specific user is performed by an electronic health records storage system.

16. The method of claim 15, further comprising:
receiving, by the electronic health records storage system, a subsequent data package;
using the data item string to decode data from the subsequent data package; and
storing the decoded data from the subsequent data package as an electronic health record on a non-transitory computer-readable memory of the electronic health records storage system.

17. The method of claim 12, further comprising:
identifying a plurality of chaff points from the plurality of data pairs from the data package, wherein the plurality of chaff points include points that do not correspond to any of the identified signal features from the physiological signal; and disregarding the identified chaff points while reconstructing the polynomial equation.

18. The method of claim 12, wherein reconstructing the polynomial equation based on the subset of data pairs includes reconstructing the polynomial equation using LaGrangian interpolation.

\* \* \* \* \*